United States Patent [19]
Kidder

[11] Patent Number: 4,792,333
[45] Date of Patent: Dec. 20, 1988

[54] UNIT DOSE DRUG PACKAGE AND ADMINISTERING DEVICE

[75] Inventor: Samuel W. Kidder, Wheaton, Md.
[73] Assignee: Strawdose, Inc., Wheaton, Md.

[21] Appl. No.: 926,666
[22] Filed: Nov. 4, 1986
[51] Int. Cl.[4] .................... A61M 37/00
[52] U.S. Cl. .................... 604/83; 604/84
[58] Field of Search .................... 604/56, 57, 59, 60, 604/82-85, 92, 77, 111, 54; 206/219, 221, 507; 383/5

[56] References Cited

U.S. PATENT DOCUMENTS

| | | | |
|---|---|---|---|
| 1,254,115 | 1/1918 | Brand | 206/217 |
| 1,534,852 | 4/1925 | Hunter | 604/84 |
| 2,436,505 | 2/1948 | Du Rall | 604/77 |
| 2,518,486 | 8/1950 | Mende | 604/60 |
| 3,366,113 | 1/1968 | Hobbs | 604/111 |
| 3,824,322 | 7/1974 | Fiorella | 426/134 |
| 3,933,304 | 1/1976 | Judd | 383/5 |
| 4,051,977 | 10/1977 | Steinfeld | 221/96 |
| 4,134,494 | 1/1979 | Wong | 206/216 |
| 4,387,809 | 6/1983 | Botzler | 206/526 |
| 4,449,631 | 5/1984 | Levenberg et al. | 206/807 |
| 4,537,308 | 8/1985 | Hollander, Jr. | 206/219 |
| 4,568,331 | 2/1986 | Fischer et al. | 604/56 |
| 4,581,013 | 4/1986 | Allen | 604/84 |
| 4,664,257 | 5/1987 | Nilson | 206/219 |

*Primary Examiner*—John D Yasko
*Attorney, Agent, or Firm*—Fay, Sharpe, Beall, Fagan, Minnich & McKee

[57] ABSTRACT

The invention provides a tamper evident package for a solid oral drug dose that, after being opened, may be used for administering the dose to a patient without removing the dose from the package. The invention also provides a method for using a package for a solid oral drug dose as an aid in administering the dose contained within the package to a patient. The method of administering the packaged drug takes advantage of the normal swallowing reflex, thus facilitating oral ingestion of the dose, and positively identifies the drug up to an including the act of drug ingestion by the patient.

16 Claims, 2 Drawing Sheets

UNIT DOSE DRUG PACKAGE AND ADMINISTERING DEVICE

BACKGROUND OF THE INVENTION

This invention relates to a tamper evident unit dose package for packaging an individual drug dose. In particular, it relates to a tamper evident package that can be opened and used as a device for administering the contained drug without removing the drug from the package.

Unit dose packaging, developed in the 1960's, provides a system of drug distribution used primarily for hospitals and nursing homes. Drug doses are packaged individually and the packages are labeled to clearly identify the drug contained within the package Using a unit dose drug packaging system decreases the amount of time required to prepare individual drug doses for patients. The system, when properly implemented, also reduces the chance of administering the wrong drug, or wrong dosage of the drug to the patient. Therefore, unit dose drug distribution systems and their variations are employed in many hospitals and nursing homes in the United States.

Unfortunately, those who administer unit dose packaged drugs do not always follow the prescribe guidelines for implementing the system. It is a common practice to prepare several patients' drug orders at one time. The preparer removes the drug dose from the unit dose package and places it in a souffle cup, which contains other drug doses for the same patient. Then, the prepared souffle cup of drug doses is presented to the patient and the contents emptied into his mouth. Subsequently, juice or water is given with instructions for the patient to swallow the doses. This procedure makes it difficult for the doses to be comfortably swallowed.

Mixing different drug doses within a souffle cup also increases the risk of administering an improper dosage to the patient. Care is taken to ensure that the correct cup is given to the right patient, but once the doses are mixed together, only experienced medical professionals, for example pharmacists, are able to positively identify and confirm that the correct drugs and dosages are contained within the cup. Checking the patient's drug order before it is ingested is important in practice, particularly in nursing homes where a variety of drugs are administered every day to different patients. In fact, the unit dose packaging system was developed to ensure that the correct drug dose is administered to the right patient. It was not envisioned that the medical professionals administering the unit dose package system would remove the doses from their packages and mix them together in a manner in direct conflict with the way the system was designed to be implemented.

An alternative method of administering the unit dose packaged drugs that avoids the difficult swallowing step encountered in the souffle cup method involves removing the dose from the package and crushing it into a powder form. The powdered drug is then mixed with the patient's food, so that it may be eaten rather than swallowed with a liquid. Apart from the bad taste experienced by eating such a mixture, this practice introduces an error in administering an accurate quantity of the drug. Crushing the drug into powder form also involves an additional step in preparing the drug for ingestion by the patient, which increases the amount of time needed to administer the drug.

In view of the practices of administering unit dose packaged drugs, it is apparent that several problems exist with the current system. Removing the doses from the package creates uncertainties in later identifying the drug after it has ben unpackaged. Mixing several doses together in a souffle cup makes it difficult for the patient to swallow the doses. Further, to alleviate the swallowing problem, the practice of crushing the dose to powder form creates possible inaccuracies in administering the correct dosage to the patient in addition to increasing the amount of time spent per patient in administering the drug. Therefore, a need exists for a unit dose package that can be used in a packaging and distribution system that when implemented eliminates the need for the above practices.

The pharmaceutical industry, is currently faced with an even greater problem. Several widely publicized incidents of random drug package tampering have led to the tragic deaths of innocent victims, who have unknowingly ingested drugs that have been tampered with. Up to this point, packages had been designed with little regard for warning the consumer that the contents of the package have been tampered with. In response to drug tampering incidents, tamper evident packages have been utilized in the industry to offer more protection for the consumer by providing a package having a safety seal or the like that if broken indicates the package may have been tampered with.

Even though a system of tamper evident packaging has been implemented, some types of drug forms, such as capsules, have still been tampered with. It is very difficult to determine if an individual capsule has been opened and a contaminate placed within the capsule. As a result, it has been proposed that a seal be applied to each individual capsule so that the consumer is able to determine if the individual capsule has been tampered with by examining the seal. If the seal is in place then the drug dose has not been tampered with. Providing individual seals for each capsule is expensive and involves retooling the capsule manufacturing machinery. Absent the implementation of effective protective measures, however, the pharmaceutical industry may be faced with a large group of consumers unwilling to purchase drugs that are packaged in capsule form. Therefore, if the pharmaceutical industry does not react to protect the consumer with improved drug packaging, the market for some drug forms particularly capsules, will diminish. A practical design for tamper evident drug packaging, particularly for capsules, needs to be developed. Preferably, this design should provide a package that can be produced at a minimum of cost, since any additional costs will be passed onto the consumer.

The tampering that has occurred to date has involved over-the-counter packaged drugs. A drug dose is removed from the package, tampered with, and replaced within the package in its tampered form. The consumer then, not noticing any evidence that the package has been tampered with, ingests the medication. In the use of over-the-counter drugs, the drug is removed from the package and immediately ingested. However in hospitals and nursing homes, the drug doses are removed from the packages usually at a nursing station, and later administered to the patient. Presently, tampering in hospitals and nursing homes is not a problem, but once the drug dose is removed from the package, the dose is subject to possible tampering. Therefore, the medical professionals in hospitals and nursing homes are confronted with the possibility of someone tampering with the drug dose after it has been unpackaged and before it has been administered.

Several attempts have been made to solve the above mentioned problems. For example, to alleviate the problems of administering drug doses, a pill douser is disclosed in U.S. Pat. No. 2,436,505 that includes a bowl and tube extending downwardly from the bowl that is intended to be placed in a quantity of liquid. The bowl supports a pill or tablet. In use the mouth is engaged about the periphery of the bowl for drawing a liquid through the tube and into the user's mouth with the pill or tablet. The douser, however, is not used for packaging the drug, and the drug dose must still be transferred from the package to the douser with the resultant possibility that the dose may be tampered with in the interim.

SUMMARY OF THE INVENTION

The invention provides a package for a solid oral drug dose that, after being opened, may be used for administering the dose to a patient without removing the dose from the package. The invention also provides a method for using a package for a solid oral drug dose as an aid in administering the dose contained within the package to a patient. The method of administering the packaged drug takes advantage of the normal swallowing reflex, thus facilitating oral ingestion of the dose.

It is an object of the invention to eliminate the intermediate step of removing the drug dose contained within a unit dose package for administering the dose to the patient. The method of the invention comprises opening the package and using the opened package for delivering the drug dose directly into the mouth of the patient. After opening the package at both ends, one end is placed in a liquid and the other end in the patient's mouth. The patient then draws the liquid through the package for delivering the dose and liquid into the mouth. This triggers the natural swallowing reflex and allows for easy swallowing of the liquid and the drug dose entrained within the liquid flow.

The package of the invention contains a solid oral drug dose that is completely identified by a label. The label contains at least the name, strength and dosage of the drug dose contained within the package. Additional information, such as the drug expiration date can optionally be identified on the drug package label. Positive labeling of the drug dose package leads to the attainment of an important objective of the invention. Since the dose is never removed from the labeled package and the package is used for delivering the drug dose directly into the patient's mouth, it is possible to positively identify the drug dose while it is being administered and therefore immediately before it is ingested.

As a result of using the package and method of the invention, a consistent and accurate dosage can be orally administered to a patient easily and efficiently without the need to remove the drug from the package or change it to a powdered form for mixing it with the patient's food. The need for souffle cups is also eliminated and complete identification of the drug is possible even during the administration of the drug.

It is a further object of the invention to provide a tamper evident package that is hermetically sealed and moisture impermeable. In a preferred embodiment, the package is constructed to have a tubular cross-sectional shape. The tubular walls are sufficiently thick to be suitable moisture barriers and sufficiently resilient so that upon cutting the ends of the package the walls are collapsible, but return to their original tubular shape after being cut. It is further preferred that the tubular walls are sufficiently stiff to withstand a suction force created by a user without collapsing the tubular shape while allowing liquid to flow through the package entraining the solid substance within the flow.

It is preferred that the tubular package have a circular cross-sectional shape for containing capsules, or a generally rectangular cross-sectional shape for containing tablets. The contained drug is supported within the package adjacent the end of the package which is intended to be placed within the user's mouth. Suitable supports include a screen positioned between the walls of the package or a piece of fibrous, porous material wedged between the walls of the package. In a preferred embodiment, a portion along the length of the tubular package can be deformed inwardly to provide an inwardly extending circumferential or peripheral constriction for supporting the packaged dose. Alternatively, the tubular package can have a gooseneck portion including a trap for supporting the drug dose, wherein the drug dose can be provided in powdered form or crushed to powder from a tablet form without removing the drug from the package. The ends of the package are sealed to provide a hermetically sealed package, the solid dose being confined within the portion of the package bound by one of the sealed ends and the supporting portion of the package. The ends can be formed by bonding the oppositely facing sidewalls of the package together.

It is a further object of the invention to provide a tamper evident package wherein the bonded end portions of the package can be coated with a dye containing coating after the bonded seal has been formed. Thereafter, should the bonded joint be tampered with, evidence of the tampering will be readily noticeable. For example, should the bonded joint be cut for gaining access to the interior of the package, the dyed end portion would be removed from the package indicating that the original sealed package had been tampered with. If a new bonded joint is formed to reclose the package, the newly formed joint would not include the dye coating, which would alert the user to the possibility that the package has been tampered with.

DETAILED DESCRIPTION OF THE PREFERRED EMBODIMENTS

Figure 1:
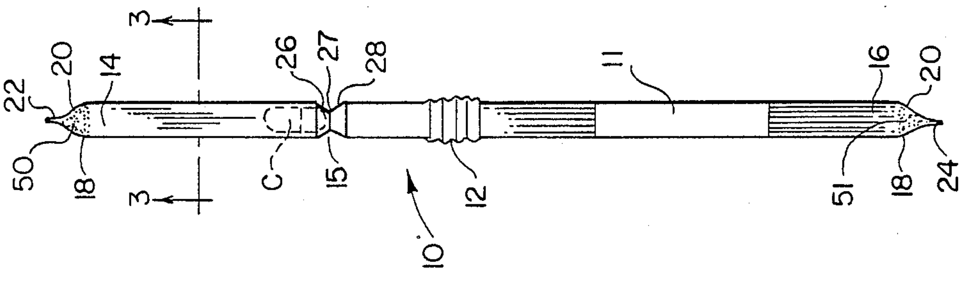
FIG. 1 is a side view of the combination package and administering device.

FIG. 1 discloses a package and administering device constructed according to one embodiment of the invention. The package has an overall tubular shape, generally indicated by reference numeral 10. The package is provided with opposite ends 14 and 16. Optionally, a flexible intermediate accordion-like portion 12 can be incorporated into the side wall structure of the package.

The package is sealed at ends 14 and 16 by providing a bonded end joint at 22 and 24 respectively. Oppositely facing sidewalls 18 and 20, as seen in FIG. 1, are pressed toward one another at the ends of the package. This causes the generally circular cross sectional shape of the package to flaten out as clearly indicated in FIG. 2. Bonded joints 22 and 24 can be formed, for example, by adhesively bonding oppositely facing sidewalls 18 and 20 together. Preferably, the bonded joints are formed by applying heat and pressure to sidewalls 18 and 20 to melt the interior surfaces of the sidewalls to form a fusion bonded joint.

The integral tubular structure 10 and bonded joint ends 22 and 24 provide a hermetic package that is suitable for containing a solid oral drug dose. A label 11 is provided to completely identify the name, strength, and dosage of the drug contained within the package.

In the embodiment of the package and administering device disclosed in FIG. 1, a capsule drug form C is contained within the package. Capsule C is positioned within the package between end 14 and an inwardly extending circumferential or peripheral constriction generally indicated at 15. It is preferred that the clearance between the outer diameter of capsule C and the inner diameter of tubular package 10 be approximately 0.5 mm. Constriction 15 comprises a throat portion 27 formed between inwardly sloping wall portions 26 and 28 as seen in FIG. 1. It is preferred that the constriction have a surface depth of approximately 1 mm.

Figure 2:
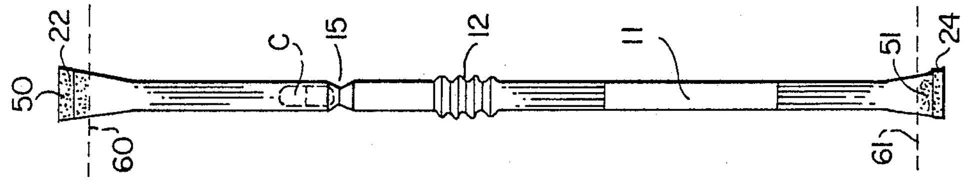
FIG. 2 is another side view of the combination package and administering device of FIG. 1.

As seen in FIGS. 1 and 2, throat 27 is of a diameter sufficient to prevent capsule C from sliding past constriction 15. Therefore, constriction 15 confines capsule C to the upper portion of the package.

In a preferred embodiment, package 10 is constructed of an organic polymer, such as polyethylene or another suitable thermoplastic synthetic resin. The thickness of the walls are sufficient to provide a barrier against moisture. Polyethylene is also preferred because it is readily deformable through the application of heat and pressure. For example, constriction 15 can be formed by encircling the sidewalls of the package with a heated dye. Also, polyethylene is a preferred material of construction since the bonded end portions 22 and 24 can be formed by applying heat and pressure directly to the sidewalls 18 and 20 respectively to form a fusion bonded joint. The fusion bonded joint completes the unitary, integral form of the package. The package is formed from one piece of material and is hermetically sealed at its ends by integrally joining the walls of the package together.

The package constructed according to the preferred embodiment of this invention is useful in providing tamper evidence. The unitary, integral construction of the package allows for quick visual inspection of the entire package. Once the package is broken into, it cannot be easily reclosed or repaired without noticeable evidence of the repair having been made.

The most common method of tampering with a package involves opening the package and resealing the package in the same manner in which is was originally sealed. As seen FIG. 2, the package of the invention is intended to be opened by cutting off the ends along lines 60 and 61. This would remove the bonded end joints 22 and 24 from the package thus opening the package. As indicated at 50 and 51, the ends of the package are coated with a dye containing coating. Cutting end portions 22 and 24 off from the package also removes the coated end portions. Therefore, should someone attempt to reseal the package, the resultant sealed package would not have the coated end portions 50 and 51. This would alert the user of the package to the possibility that the package has been tampered with.

The dye containing coating can be a paint or a colored vinyl coating. Alternatively, the coating could be translucent or clear. Further, a reference line positioned along lines 60 and 61 could be used to indicate to the consumer the area of the correct amount of coating that should be visible if the package has not been tampered with. Instructions for the consumer explaining how to detect evidence of tampering of the package can be supplied on label 11. Further, should the package be opened and reclosed by someone attempting to tamper with the contents, the overall length of the package would be shortened. This would provide an additional indication that the package has been tampered with. Alternatively, in place of the dye containing coating, an adhesively boned thin layer of foil could be applied to the ends to serve the same purpose as the coating.

Figure 3:
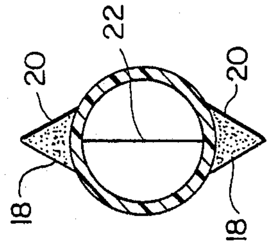
FIG. 3 is a section view taken along line 3—3 of FIG. 1.
Figure 4:
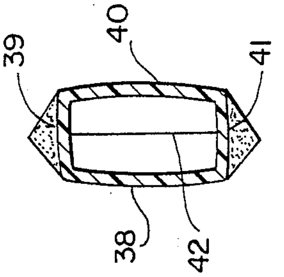
FIG. 4 is a section view taken along line 4—4 of FIG. 5.
Figure 6:
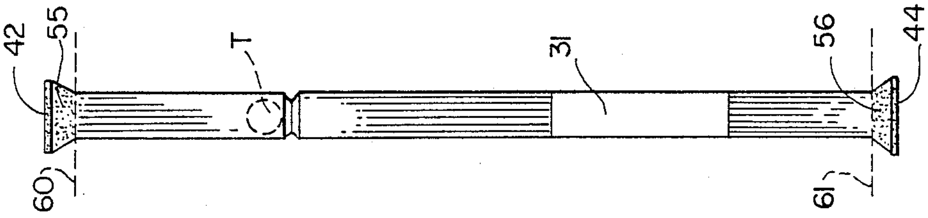
FIG. 6 is another side view of the package and administering device of FIG. 5.
Figure 5:
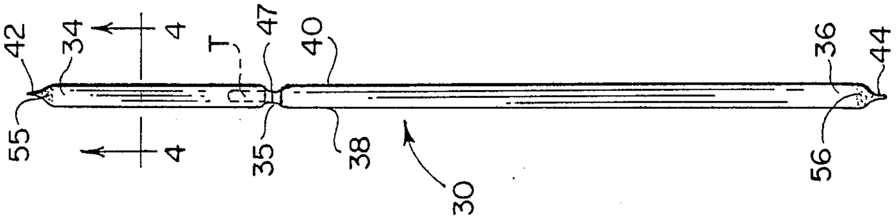
FIG. 5 is a side view of a package and administering device constructed according to another embodiment of tee present invention.

Discussion of the package and administering device has been made with reference to FIGS. 1–3, wherein the package is intended to contain a capsule form of a drug dose. In FIGS. 4–6, an alternative embodiment of the package is disclosed, wherein the cross sectional shape is generally rectangular.

As seen in FIG. 5, a generally tubular package 30 is shown. Package 30 has opposite end walls 42 and 44 and contains a tablet T. Tablet T is positioned between end 42 and a peripheral constriction 35 extending inwardly from the sidewalls of the package.

As seen in FIG. 4, the package has sidewalls 38, 39, 40 and 41. The generally rectangular cross sectional shape of package 30 matches the shape of most commercially available tablets.

As seen in FIG. 6, sidewalls 38 and 40 are flattened to form bonded end joints 55 and 56, which can be adhesively bonded together or fusion bonded together. In a preferred embodiment, the package is constructed of polyethylene and the sealed ends are fusion bonded joints.

Package 30 is provided with constriction 35 having a throat portion 47. Throat 47 is formed from inwardly extending sidewall portions not referenced by number for clarity.

Package 30 is also provided with tamper evident features, such as dye containings coating 55, 56, which are added to the exterior of the package to cover bonded joints 42 and 44.

Figure 7:
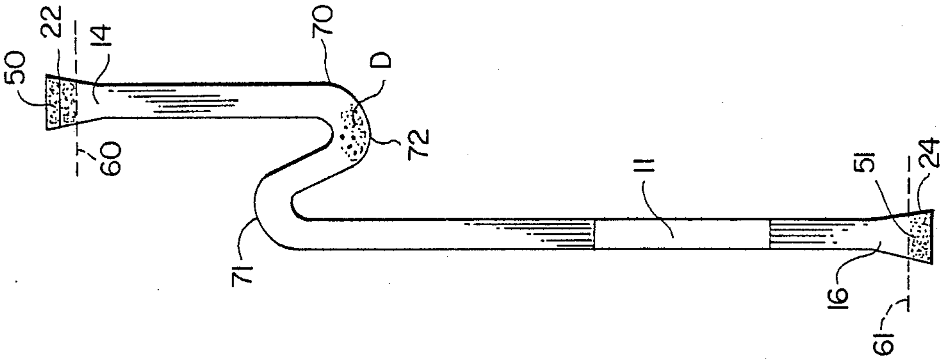
FIG. 7 is a side view of another embodiment of the package and administering device constructed according to the present invention.

In FIG. 7, another embodiment of the tamper evident package and administering device of the invention is shown. The package of FIG. 7 is similar to the embodiment discussed with reference to FIGS. 1–3. As seen in FIG. 7, the contained drug can be provided in a powdered form. The tubular package has intermediate bends 70 and 71 formed in the shape of a gooseneck, to provide a trap at 72. The powdered substance is supported within the trap at 72 adjacent end 14, which is intended to be inserted into the user's mouth.

In the preferred use of the package disclosed in FIG. 7, a solid tablet is positioned within the package adjacent end 14 so that it rests within bend 70, preferably at trap 72. When it is desired to administer the tablet to a patient, the administering person crushes the tablet by use of a roller pin, or the back of a spoon. Care is then taken in handling the package to ensure that the contained powdered form of the tablet remains confined within trap 70. The package is then opened and used as an administering device as discussed hereinafter.

It is preferred that the package of FIG. 7 be constructed of polyethylene. Polyethylen is resilent enough to flex during the step of crushing the tablet without failing to return to its original shape after the tablet has been crushed. The bends 70 and 71 can be formed during an extrusion process or the package can be injection molded. Alternatively the tube can be constructed with at least one accordian like portion so that the bends 70 and 71 can be formed in the package immediately prior to crushing the contained tablet.

FIGS. 2, 6 and 7 show that the package constructed according to the preferred embodiments of the invention can be opened by cutting along lines 60 and 61 respectively. Once opened, the package can be used as an administering device for delivering the contained drug dose directly into the mouth of the patient. Therefore, removal of the drug dose from the package for administering the dose to the patient is eliminated. This eliminates a step in administering the drug and decreases the chance that the drug dose will be tampered with during the interim period between the time the package is opened and the dose is administered to the patient.

Figure 8:
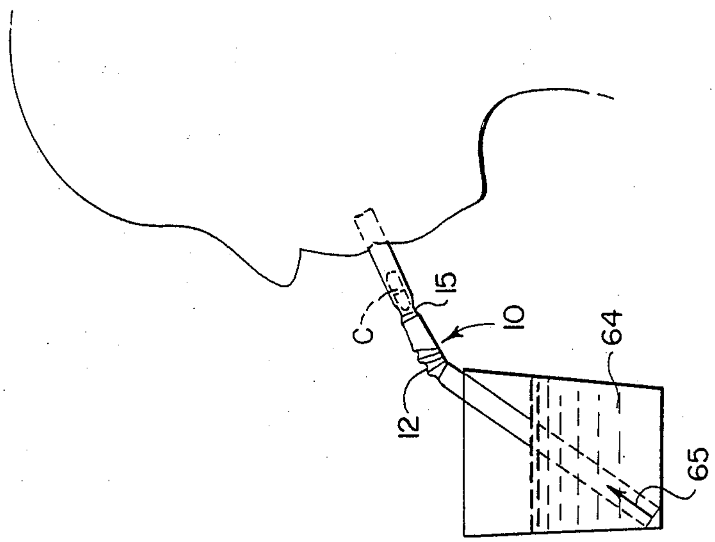
FIG. 8 is a side view of the package of FIG. 1 being used as an administering device by a user, shown schematically in profile.

FIG. 8 schematically depicts a patient using the package of FIG. 1 for delivering capsule C directly into the mouth from the package. One end of the package is positioned within the mouth and the other end is positioned within a cup of liquid, generally indicated at 64. Flexible portion 12 is manipulated to allow for the user to comfortably use the device from a sitting position, if desired.

Constriction 15 supports capsule C above the surface of the liquid contained within the cup. The inner diameter of throat 27 is of a dimension sufficient to allow passage of the liquid through constriction 15 when the patient sucks on the package. Perferably, the package has a resilience sufficient to withstand the force of the suction created by the patient.

As the patient sucks on the open package, liquid is drawn into the package as indicated by arrow 65. The liquid travels upwardly under the force of the suction exerted by the patient. The liquid flow passes through throat 27 and is concentrated on the bottom of capsule C to force the capsule upwardly through the package, entraining the capsule within the flow of the liquid. The dose then enters the mouth or oral cavity of the patient with a quantity of fluid.

As with any drinking action, the patient automatically limits the amount of fluid taken into the oral cavity. When a sufficient amount of fluid is collected the patient swallows the fluid and the dose, which easily flow together down the esophagus. The patient may then take another swallow of fluid so that the dose is thoroughly washed down the esophagus. Sometimes in actual use, the patient needs to align or orient the dose in his mouth before swallowing. This is easily accomplished with the tongue as the dose and the liquid are present together in the mouth, the dose is prevented from sticking to the mouth.

Thus, it is understood that the invention provides a simple but unique package for protecting a drug dose and for providing a device for administering the dose directly to the patient without the need for first removing the dose from the package.

What is claimed is:

1. A device for containing and orally administering as solid substance comprising:

tubular means having opposite ends and first and second portions integrally formed with said tubular means for containing the solid substance and for delivering the solid substance to a user's oral cavity with a fluid that is drawn through said tubular means from one of said ends to the other of said ends;

said tubular means having supporting and confining means separating said first portion and said second portion for supporting the solid substance adjacent said other of said ends and for confining the substance in said first portion, said supporting and confining means including a passageway therethrough for free fluid flow and said second portion having end portion means for allowing direct immersion of said second portion within a reservoir of a fluid that is to be drawn into and through said tubular means; and said ends being hermetically sealed such that the solid substance is sealed within said tubular means when said device is used as a package; and said ends being openable such that fluid flows between each of said ends through said supporting and confining means when said device is used as an administering device, whereby said device remains a package until said ends are opened whereupon said device is used as an administering device for delivering the solid substance contained within the device directly into the user's mouth.

2. The device as claimed in claim 1, further comprising tamper evidence means comprising a dye containing coating applied to each of said ends, whereby the absence of said dye coating indicates said device has been tampered with.

3. The device as claimed in claim 1, further comprising:

said tubular means being a tube having a sidewalls and a generally circular cross-sectional shape having an inner diameter; and said supporting and confining means including a constriction of said sidewalls projecting inwardly such that said construction supports the solid substance.

4. The device according to claim 3, wherein said constriction is a circumferential constriction form of a capsule.

5. The device according to claim 2, wherein said device is constructed of polyethylene and each of said ends comprises fusion bonded joints formed between said sidewalls of said tube.

6. The device according to claim 1, further comprising:

said tubular means being a tube having a generally rectangularly cross-sectional shape and having oppositely facing sidewalls; and said supporting and confining means being an inwardly extending constriction such that said constriction and said rectangular cross-sectional shape are adapted to receive the solid substance in tablet form.

7. A method for packaging a solid substance within a package and for administering the solid substance from said package, comprising the steps of:

providing a package for the solid substance having tubular means including opposite ends and side walls for containing the substance;

supporting the substance within a first portion of said tubular means adjacent one of said ends;

hermetically sealing each of said ends of said tubular means to provide a hermetically sealed package;

opening said package to use said package for administering the solid substance contained within said package by opening each of said ends for establishing a fluid passageway between said ends through which a fluid can flow from said other end to said one end;

using said open package as an administering device for delivering the solid substances contained within said package to a user by positioning said one end within the mouth of a user and positioning said other end in fluid communication with a supply of liquid; whereby the user draws the liquid through said tubular means from said other end to said one end for entraining the solid substance within the flow of fluid through said tubular means for delivering the solid substance with the fluid directly into the user's oral cavity.

8. The method according to claim 7 further comprising the steps of:

providing said package with tamper evident means comprising applying a dye coating to each of said ends for indicating to the user that said ends have been sealed by the manufacturer.

9. The method according to claim 8, further comprising the steps of:

constructing said package from a thermoplastic resin; and forming said hermetically sealed ends by applying heat and pressure to said sidewalls to form a fusion bond between said sidewalls.

10. The method according to claim 8, further comprising the step of providing said package with said tubular means having a circular cross-sectional shape for containing a substance in the form of a capsule.

11. The method as claimed in claim 8, further comprising the step of providing said tubular means with a generally rectangular cross-sectional shape for accommodating a substance in the form of a tablet.

12. The device as claimed in claim 1, wherein said supporting and confining means comprises said tubular means having a gooseneck shape portion having a trap for the solid substance, such that the solid substance can be crushed within said package before said package is opened and further such that the crushed solid substance is supported by said trap until the fluid is drawn through the tubular means whereupon the crushed solid substance is entrained within the flow of the fluid.

13. A method according to claim 7, further comprising the step of providing said package with said tubular means having a circular cross-sectional shape for containing the substance in the form of a capsule.

14. A method as claimed in claim 7, further comprising the step of providing said tubular means with a generally rectangular cross-sectional shape for accommodating the substance in the form of a tablet.

15. The method according to claim 7, further comprising:

providing said tubular means as a tube having side walls and a generally circular cross-sectional shape having an inner diameter;

providing a construction projecting inwardly from said side walls for said supporting of the solid substance; and providing the solid substance in the form of a capsule with close tolerance between the inner diameter of said tube and the outer diameter of the capsule.

16. A package and administering device for containing and administering a solid substance, comprising:

tubular means having opposite ends for containing the solid substance in dosage form;

said tubular means having means for supporting the solid substance adjacent one of said ends;

said ends being hermetically sealed such that the solid substance is sealed within said tublar means to form said package; and each of said ends being openable such that said ends of said tubular means are opened at each of said opposite ends to form said administering device, whereby the other of said ends after being opened is placed in fluid communication with a supply of liquid and said one end after being opened is placed within the mouth of one using said administering device such that the fluid is drawn through said tubular means by the user for entraining the solid substance within the flow of the fluid through said tubular means for delivering the solid substance with the fluid directly into the user's oral cavity; and tamper evident means comprising a dye coating applied to each of said ends for indicating that said ends have been sealed by the manufacturer and not yet opened.

* * * * *